US00PP31259P3

(12) United States Plant Patent
Pierron-Darbonne

(10) Patent No.: US PP31,259 P3
(45) Date of Patent: Dec. 24, 2019

(54) STRAWBERRY PLANT NAMED 'PLARED 0822'

(50) Latin Name: ***Fragaria* x *ananassa* Duchesne ex Rozier**
Varietal Denomination: Plared 0822

(71) Applicant: Plantas de Navarra, S.A. Sociedad Unipersonal, Valtierra (ES)

(72) Inventor: Alexandre Pierron-Darbonne, Pamplona (ES)

(73) Assignee: Plantas de Navarra, S.A. Sociedad Unipersonal, Valtierra, Navarra (ES)

( * ) Notice: Subject to any disclaimer, the term of this patent is extended or adjusted under 35 U.S.C. 154(b) by 0 days.

(21) Appl. No.: 15/932,844

(22) Filed: May 4, 2018

(65) Prior Publication Data

US 2019/0116701 P1 Apr. 18, 2019

(30) Foreign Application Priority Data

Oct. 13, 2017 (QZ) ..... PBR 2017/2579

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209, 208
CPC ..... A01H 5/08; A01H 5/0893; A01H 6/74; A01H 6/7409; A01H 5/0831
See application file for complete search history.

(56) References Cited

U.S. PATENT DOCUMENTS

PP16,228 P3 * 1/2006 Shaw ..... A01H 6/7409 Plt./209

* cited by examiner

*Primary Examiner* — June Hwu
(74) *Attorney, Agent, or Firm* — Knobbe, Martens, Olson & Bear, LLP

(57) ABSTRACT

Described is a new and distinct strawberry variety with varietal denomination 'Plared 0822', characterized by a combination of traits which include, but are not limited to, inflorescence that appears above the foliage, larger size of calyx relative to corolla and abundant production of medium to large-sized medium red colored, conical shaped, and firm fruits, with medium red colored flesh, with very early time of flowering and ripening. 'Plared 0822' is a fully remontant variety.

16 Drawing Sheets

Botanical classification: *Fragaria* x *ananassa* Duchesne x Rozier.

Variety denomination: The new plant has the varietal denomination 'Plared 0822'.

CROSS-REFERENCE TO RELATED APPLICATIONS

This application claims the benefit of European Community Plant Variety Office Application No. 2017/2579, for a strawberry variety named 'Plared 0822', filed on Oct. 13, 2017, the entirety of which is incorporated by reference herein.

BACKGROUND

Disclosed herein is a new and distinct strawberry variety. The varietal denomination of the new variety is 'Plared 0822'. The new variety was designated by the breeder as '08.16R.124'. The new variety of strawberry was created in a breeding program by crossing two parents in Cartaya (Huelva), Spain about 7° W, 37° N, 45 feet elevation (15 meters high); in particular, by crossing as seed parent an undistributed strawberry parent designated '00-174R' (unpatented) and as pollen parent an undistributed strawberry parent designated '09-030' (unpatented). Each parent is a selection from breeder's program and has not been commercialized.

The resulting seedling of the new variety was grown and asexually propagated by Alexandre Pierron-Darbonne by runners in Segovia, Spain, 3° 59'W., 41° 22'N., 2742 feet elevation and it was successively propagated by runners first into a Screen-House, and after in the fields. Plants of the new variety were further asexually propagated and extensively tested. In order to establish and bring to health the initial head clones, mother plants that had developed several stolons were subjected to a heat treatment, or Thermotherapy, at 36° C. –37° C. for 3 to 4 weeks. After that treatment, apical meristems were cut and developed (1 apical meristem corresponding to 1 rooting plant) in a vitro culture for 5 to 6 weeks. This propagation and testing has demonstrated that the combination of traits disclosed herein which characterize the new variety are fixed and retained true to type through successive generations of asexual reproduction.

The growing period in Cartaya (Huelva), Spain, about 7° W, 37° N, 45 feet elevation (15 meters high), where the observations were made, is between about August 5 and December 31 of each year with a date of first flowering on September 10, for Fall plantation, and between about September 25 and May 20 of next year with a date of first flowering on November 1 for Summer plantation. The location where the observations were made is Cartaya (Huelva), Spain and it is believed to apply to plants grown under similar conditions of soil and climate elsewhere.

SUMMARY

Among the characteristics which appear to distinguish the new variety from other varieties are a combination of traits which include inflorescence that appears above the foliage, the flower shows a larger size of calyx relative to corolla; medium to large size fruit that is medium red colored, conical shaped, and firm, having medium red colored flesh; and very early time of flowering and ripening. 'Plared 0822' is a fully remontant variety.

The new variety 'Plared 0822' is distinguished from others cultivars by showing the inflorescence above the foliage, the flower show a larger size of calyx relative to corolla, the fruit shows a conical shape, with medium to large size, and medium red color, the fruit is firm and it shows a medium red colored flesh, it is has very early flowering and ripening times.

COMPARISON TO THE PARENTS

The new variety 'Plared 0822' is distinguished therefrom its Seed parent '00-174R' (unpatented) in that the shape of the base in the terminal leaflet of the seed parent is obtuse, the seed parent shows a dark green upper side leaf color, the flower of the seed parent shows the same size of calyx in relation to corolla, and the seed parent shows a dark red fruit color.

The new variety 'Plared 0822' is distinguished there from its pollen parent '09-030' (unpatented) in that in the pollen parent shape of base in terminal leaflet is obtuse, the pollen parent shows a dark green leaf color of upper side, the arrangement of petals in the flower of pollen parent is touching, and the fruit of pollen parent shows the same length in relation to width.

COMPARISON TO CLOSEST VARIETY

The new variety 'Plared 0822' is closest to the variety 'San Andreas' (U.S. Plant Pat. No. 19,975) but is distinguished by the following characteristics possessed by 'Plared 0822' which are different, or not possessed by, 'San Andreas' (U.S. Plant Pat. No. 19,975).

Plant of 'San Andreas' (U.S. Plant Pat. No. 19,975) shows a semi-upright growth habit, whereas 'Plared 0822' shows an upright habit.

Leaf of 'San Andreas' (U.S. Plant Pat. No. 19,975) shows an RHS green group color in the upperside (near 135 B to 135 A), whereas the new variety 'Plared 0822' shows an RHS green group color in the upperside (near 141 B to 143 A).

Terminal leaflet in 'San Andreas' (U.S. Plant Pat. No. 19,975) shows an obtuse shape of base, whereas in the new variety 'Plared 0822' terminal leaflet shows an acute shape of the base.

Position of inflorescence in relation to foliage in 'San Andreas' (U.S. Plant Pat. No. 19,975) is at same level, whereas in the new variety 'Plared 0822' the inflorescence is above the foliage.

Attitude of sepals in fruit of 'San Andreas' (U.S. Plant Pat. No. 19,975) is outwards, whereas the attitude of sepals in fruit of 'Plared 0822' is upwards. Petals are touching in the flower of 'San Andreas' (U.S. Plant Pat. No. 19,975), whereas petals are overlapping in the flower of 'Plared 0822'.

Time of beginning of fruit ripening in 'San Andreas' (U.S. Plant Pat. No. 19,975) is early, whereas time of beginning of fruit ripening in 'Plared 0822' is very early.

Differences in shape of base in the terminal leaflet of 'Plared 0822' (designated 08.16R.124) and 'San Andreas' (U.S. Plant Pat. No. 19,975) are shown in FIG. 8.

Differences in the upperside color of leaf of 'Plared 0822' (designated 08.16R.124) and 'San Andreas' (U.S. Plant Pat. No. 19,975) are shown in FIG. 5.

Differences in the arrangement of petals in the flower of 'Plared 0822' (designated 08.16R.124) and 'San Andreas' (U.S. Plant Pat. No. 19,975) are shown in FIG. 12.

Differences in attitude of sepals in fruit of 'Plared 0822' (designated 08.16R.124) and 'San Andreas' (U.S. Plant Pat. No. 19,975) are shown in FIG. 16.

These differences are maintained during the harvest season.

BRIEF DESCRIPTION OF THE ILLUSTRATIONS

The accompanying photographs show typical specimens of the new variety, designated 08.16R.124 in the illustrations, including fruit, foliage and flower, in color as nearly true as it is reasonably possible to make in color illustrations of this character.

The plants depicted in the drawings were planted September 25 in the farm of La Mogalla in Cartaya (Huelva), Spain, about 7° W, 37° N, 45 feet elevation (15 meters high).

Drawings/photographs were taken March-April (about March 25 and April 10): minimum temperate about 10 to 12° Centigrade, maximum temperate about 22 to 24° Centigrade.

Figure 1:
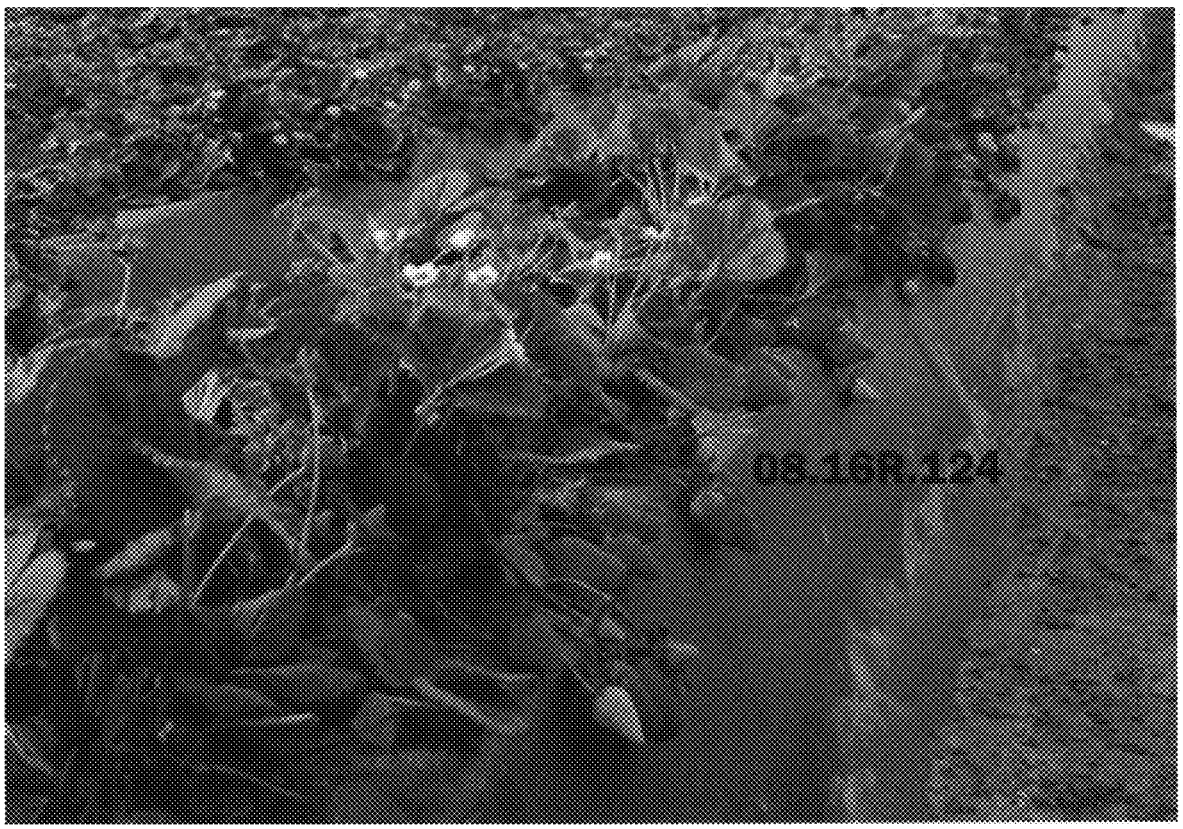
FIG. 1 shows several plants of the new variety (designated 08.16R.124) with several medium red colored and conical shape fruits.
Figure 2:
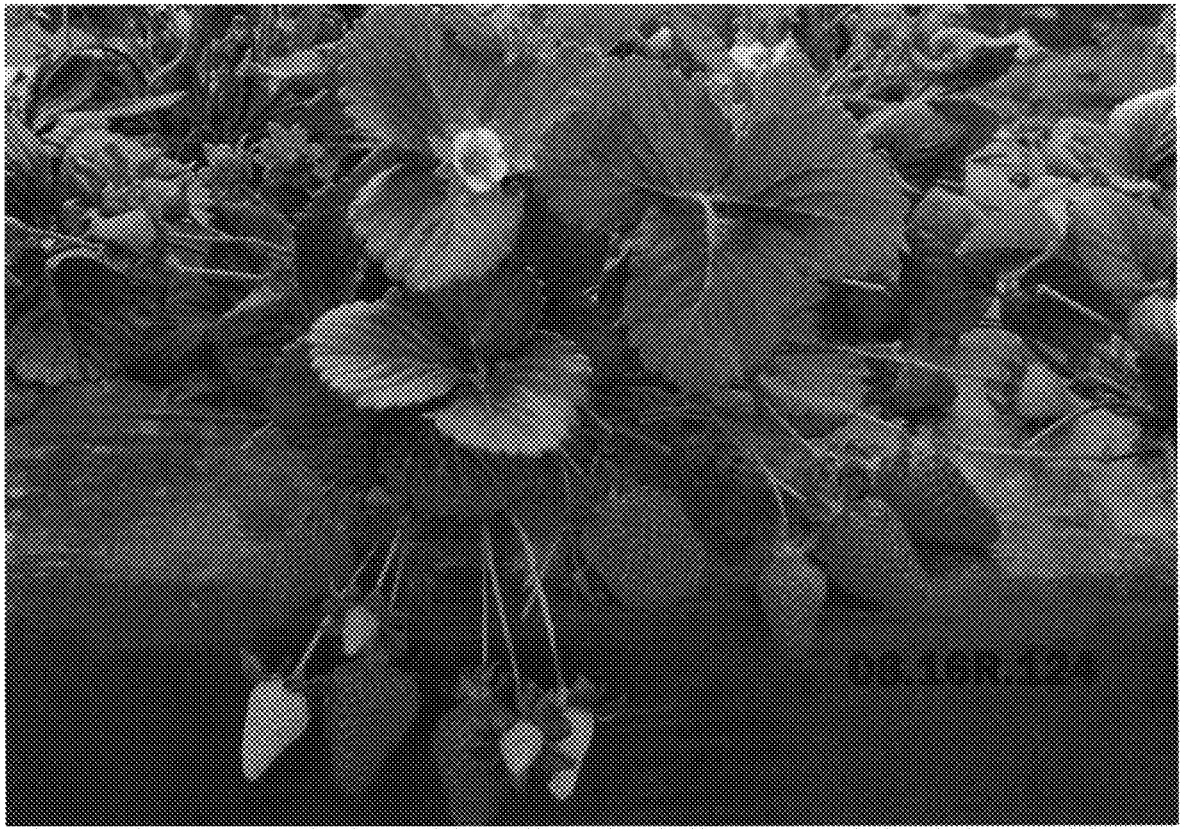
FIG. 2 shows several plants of the new variety (designated 08.16R.124) which exhibit an upright habit, a sparse density plant and the position of the inflorescence relative to foliage is above.
Figure 3:
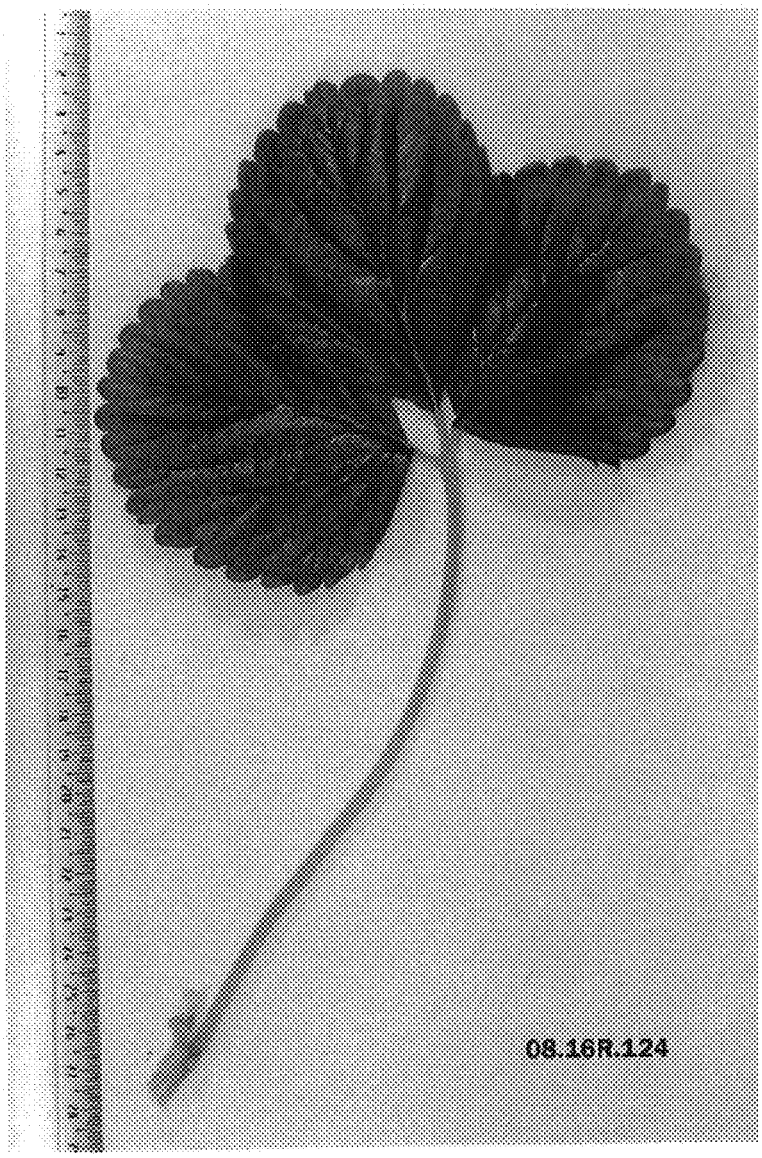
FIG. 3 shows the upperside of a complete leaf of the new variety (designated 08.16R.124). In it we can see that the leaf color of upperside is RHS green group color (near 141 B to 143 A).
Figure 4:
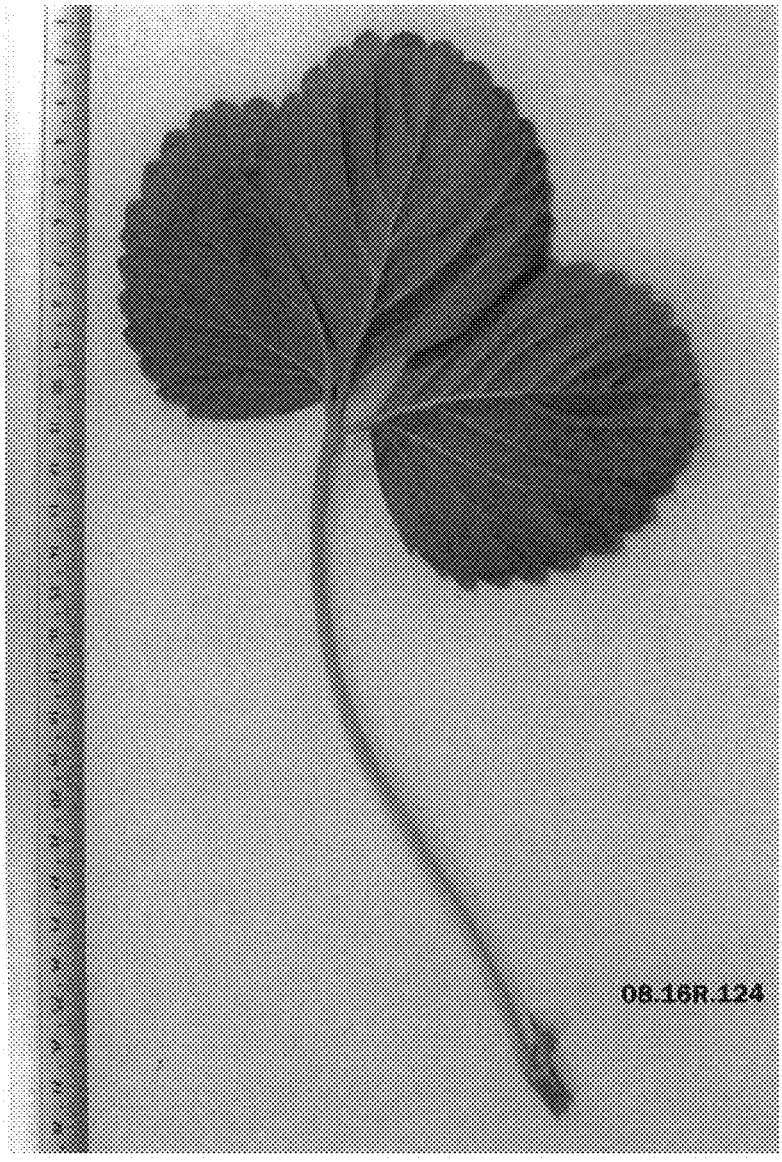
FIG. 4 shows the underside of a complete leaf of the new variety (designated 08.16R.124). The leaf color of underside is RHS yellow-green group color (near 147 C to 148 B).
Figure 5:
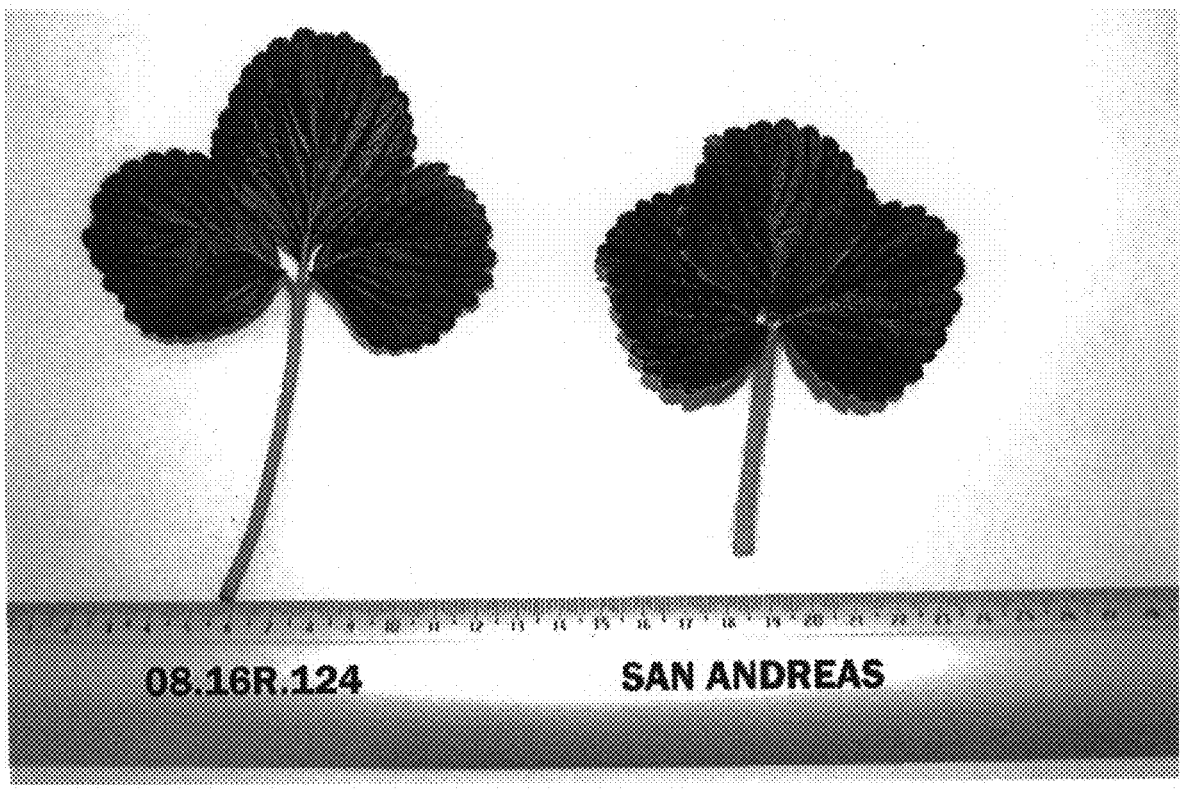

FIG. 5 shows the upperside of a complete leaf of the new variety (designated 08.16R.124), with a RHS green group color (near 141 B to 143 A), in comparison with the upperside of a complete leaf of strawberry variety 'San Andreas' (U.S. Plant Pat. No. 19,975), with a RHS green group color (near 135 B to 135 A).

Figure 6:
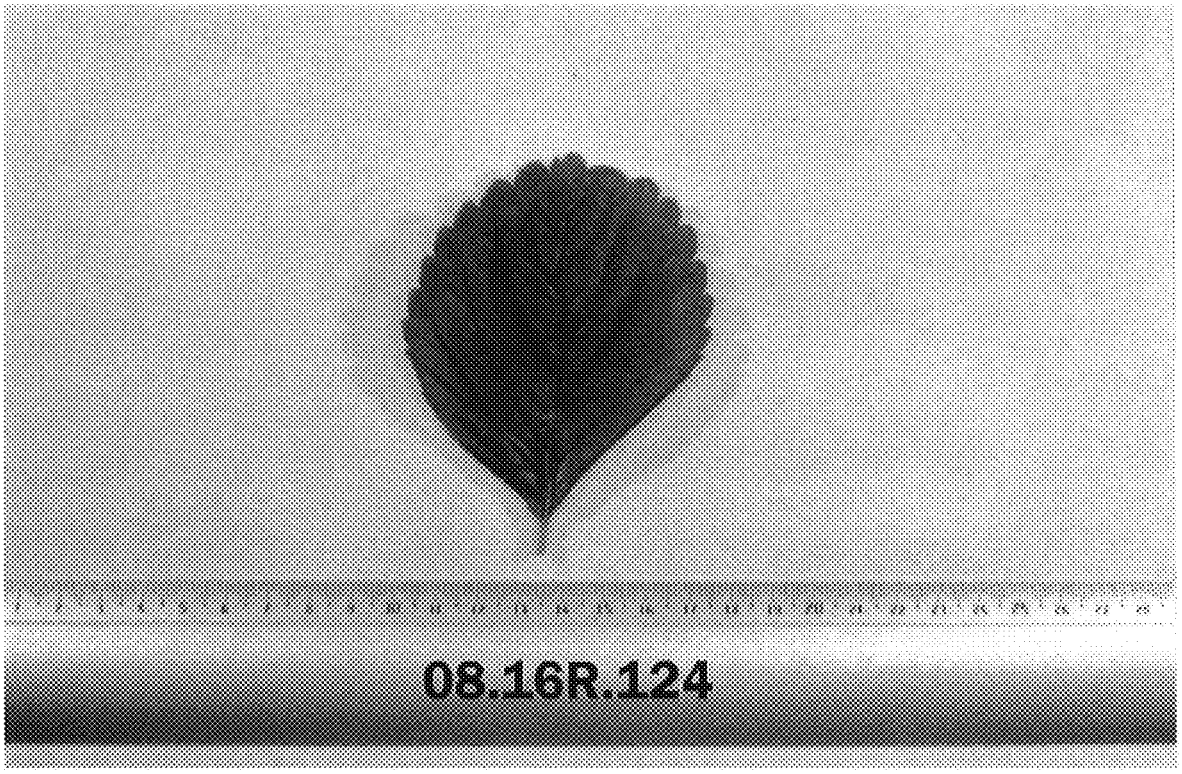
Figure 7:
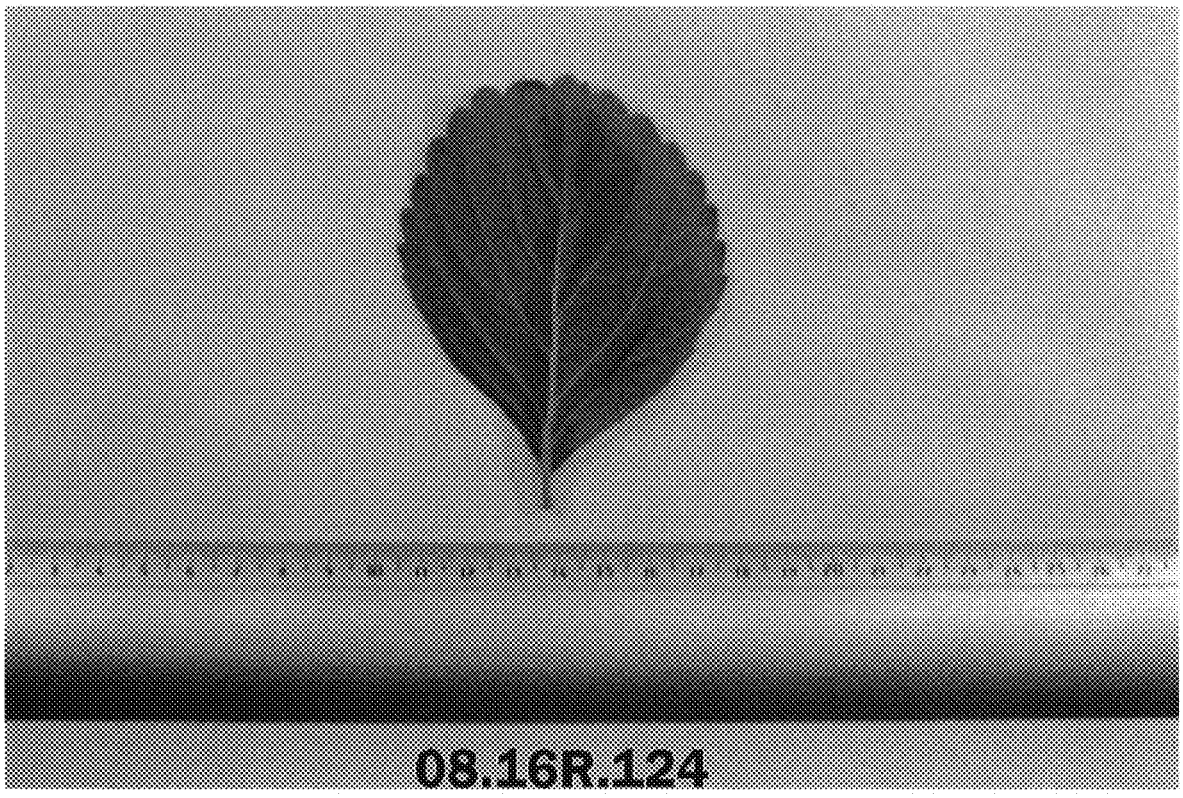

FIG. 6 and FIG. 7 show the upperside and the underside, respectively, of the terminal leaflet of the new variety (designated 08.16R.124). We can appreciate the acute shape of the base.

Figure 8:
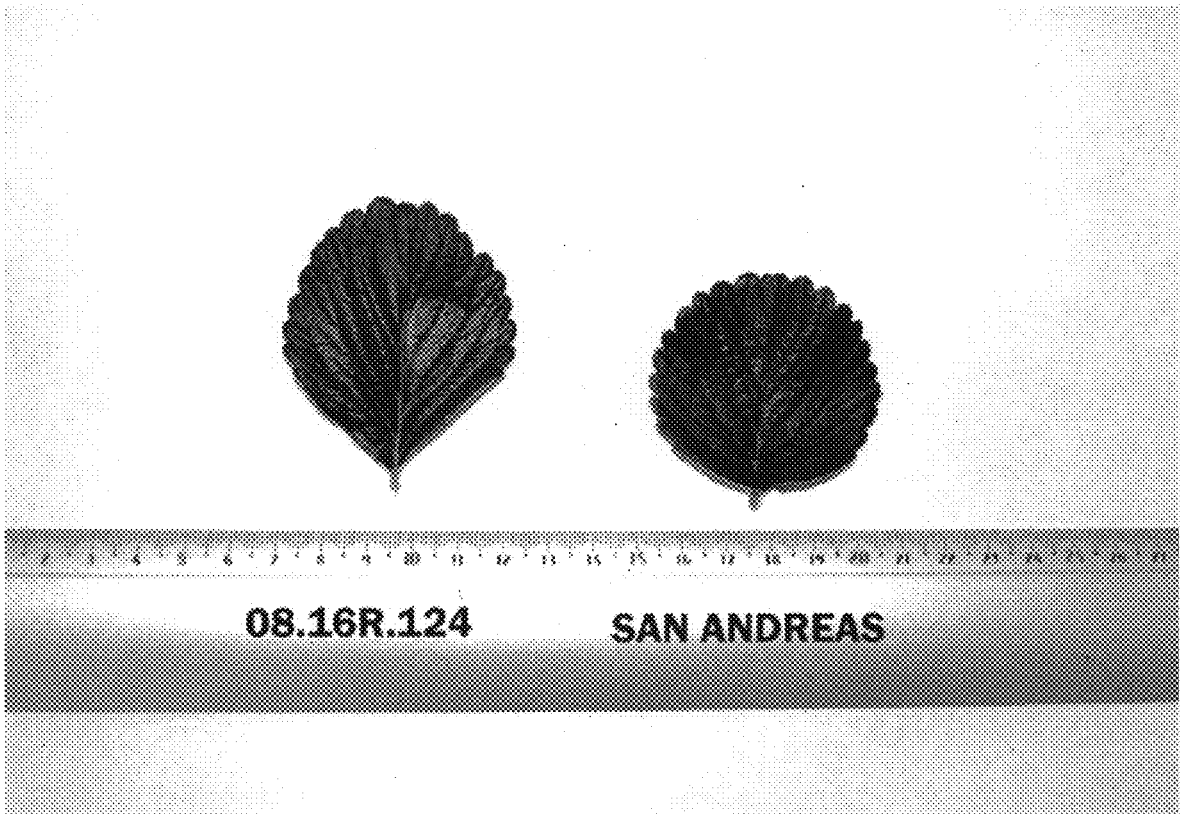

FIG. 8 shows the upperside of the terminal leaflet of the new variety (designated 08.16R.124) with an acute shape of the base, in comparison with the terminal leaflet of strawberry variety 'San Andreas' (U.S. Plant Pat. No. 19,975), with an obtuse shape of the base.

Figure 9:
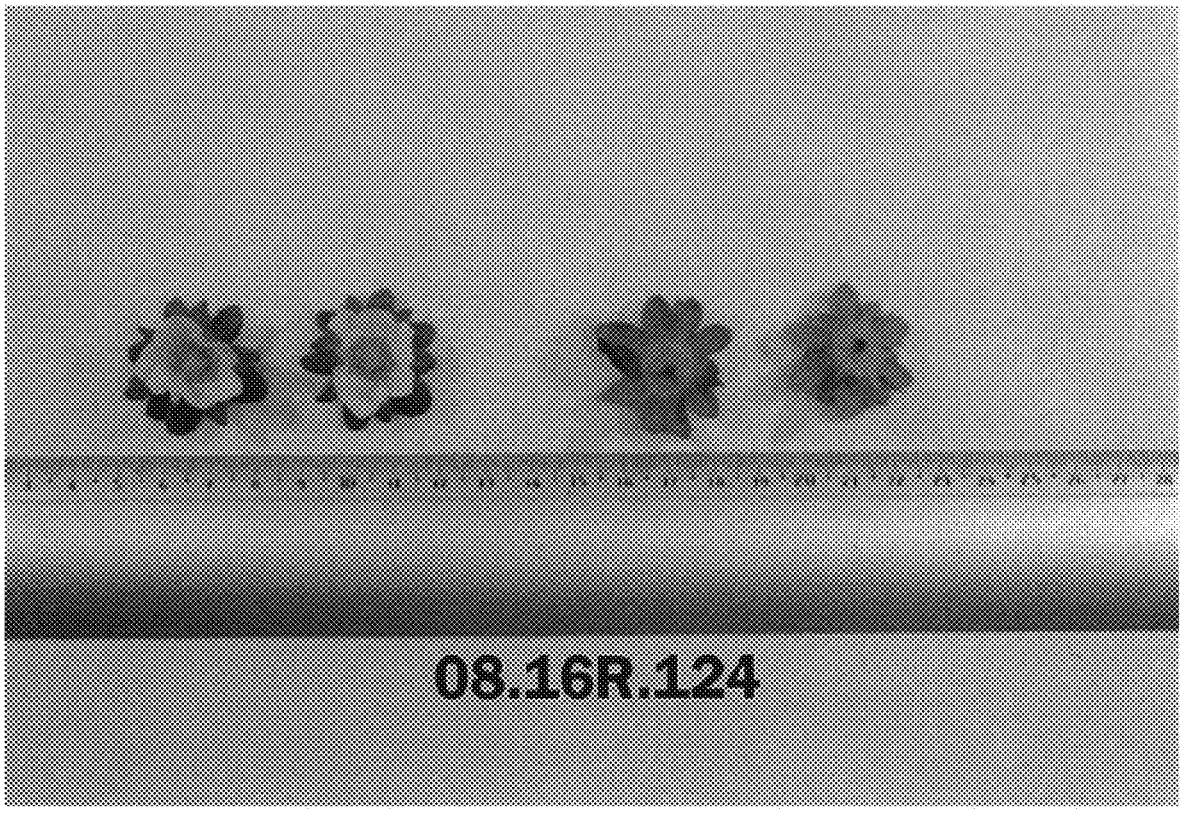

FIG. 9 shows several flowers of the new variety (designated 08.16R.124). The flowers on the left show the upper surfaces, while the flowers on right show the lower surfaces.

Figure 10:
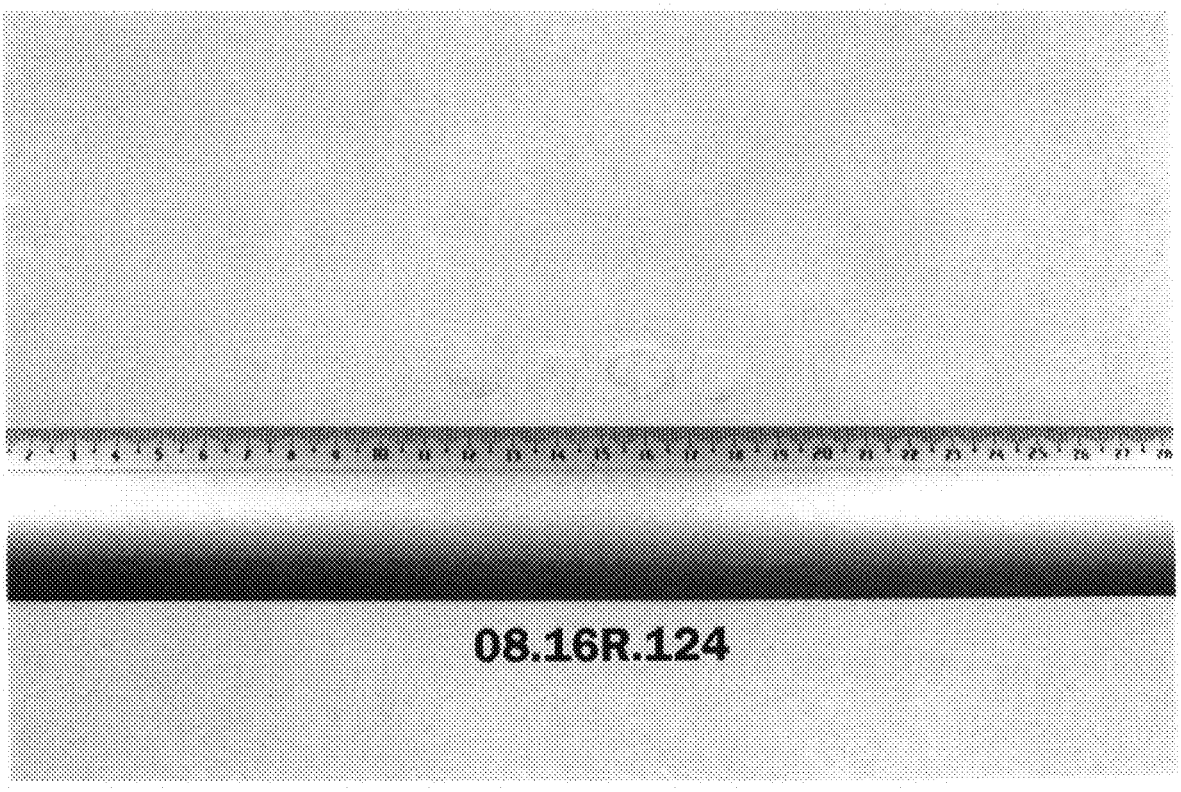

FIG. 10 shows several petals of the new variety (designated 08.16R.124).

Figure 11:
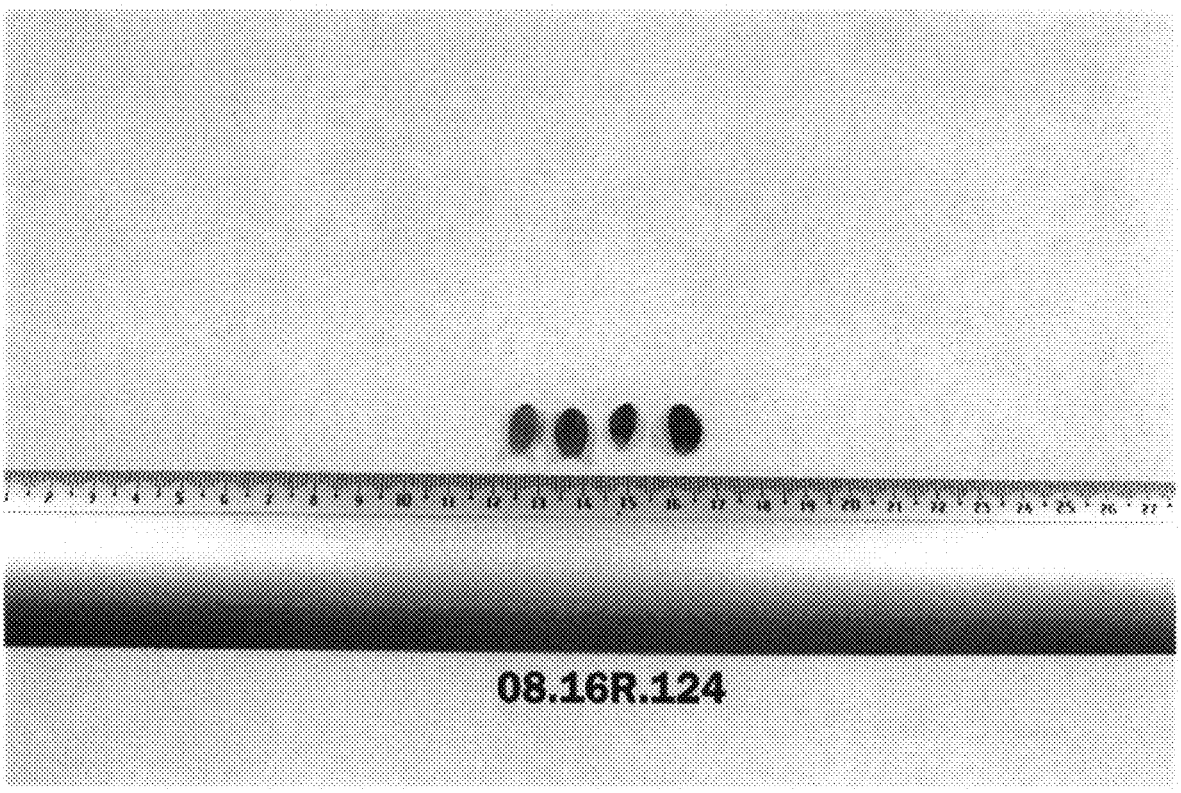

FIG. 11 shows upperside and underside of typical sepals of the new variety (designated 08.16R.124). The sepals on the left show the underside, while the sepals on right show the upperside.

Figure 12:
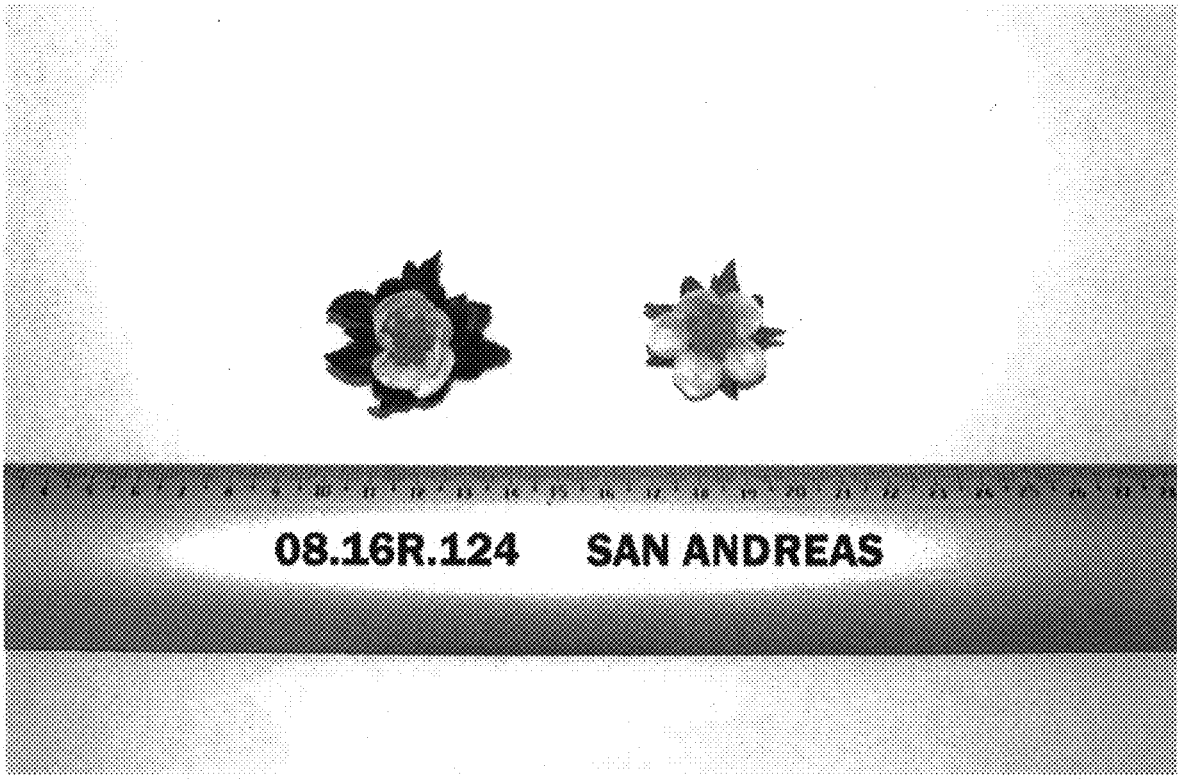

FIG. 12 shows the comparison between flowers of the new variety (designated 08.16R.124) and the strawberry variety 'San Andreas' (U.S. Plant Pat. No. 19,975). In it we can see that the arrangement of petals is touching in the flower of 'San Andreas' (U.S. Plant Pat. No. 19,975), whereas the petals are overlapping in the flower of the new variety (designated 08.16R.124).

Figure 13:
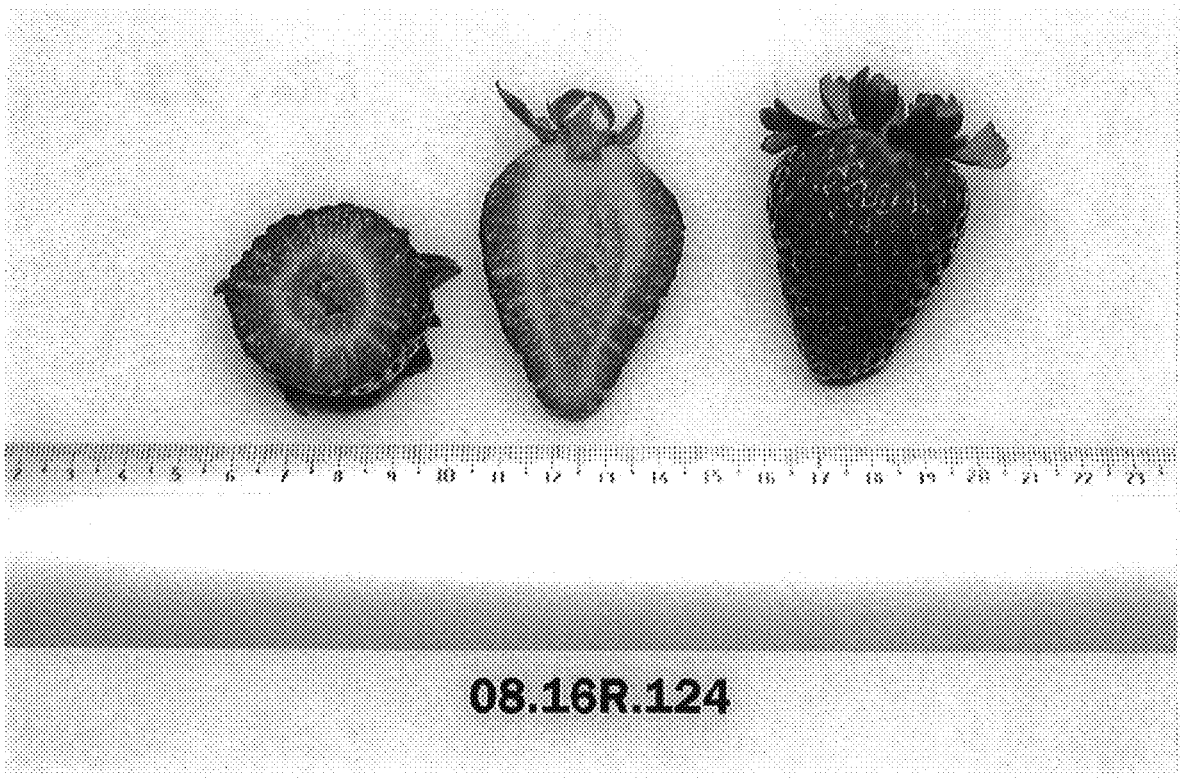

FIG. 13 shows typical fruit of the new variety (designated 08.16R.124) whole, sliced and in cross section, illustrating the typical medium red fruit color (RHS red group near 44 B to 44 A), the typical orange red flesh coloration (RHS orange-red group near 34 B to 34 A) lightening toward the center, with a small to medium hollow center.

Figure 14:
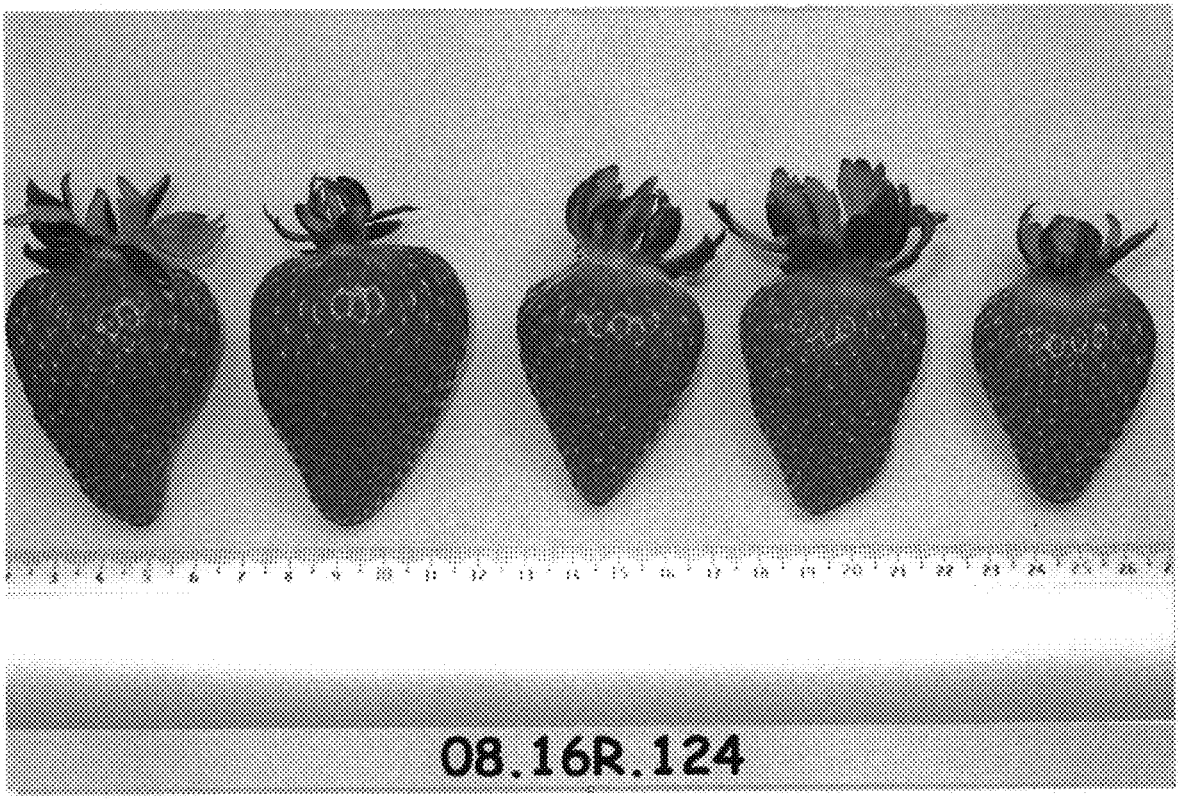

FIG. 14 shows several typical fruits of the new variety (designated 08.16R.124) illustrating the typical conical shape and medium red fruit color (RHS red group near 44 B to 44 A).

Figure 15:
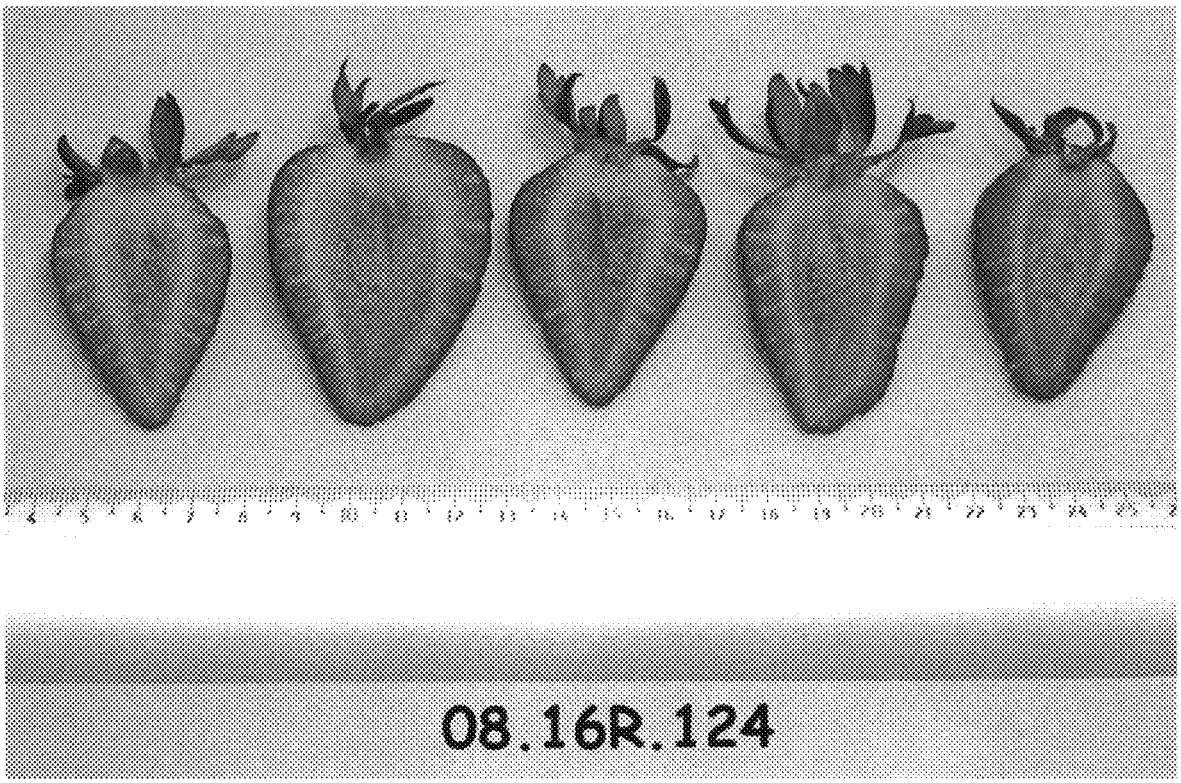

FIG. 15 shows several typical fruits of the new variety (designated 08.16R.124) in cross section illustrating the typical orange red flesh coloration (RHS orange-red group near 34 B to 34 A) lightening toward the center, with a small to medium hollow center.

Figure 16:
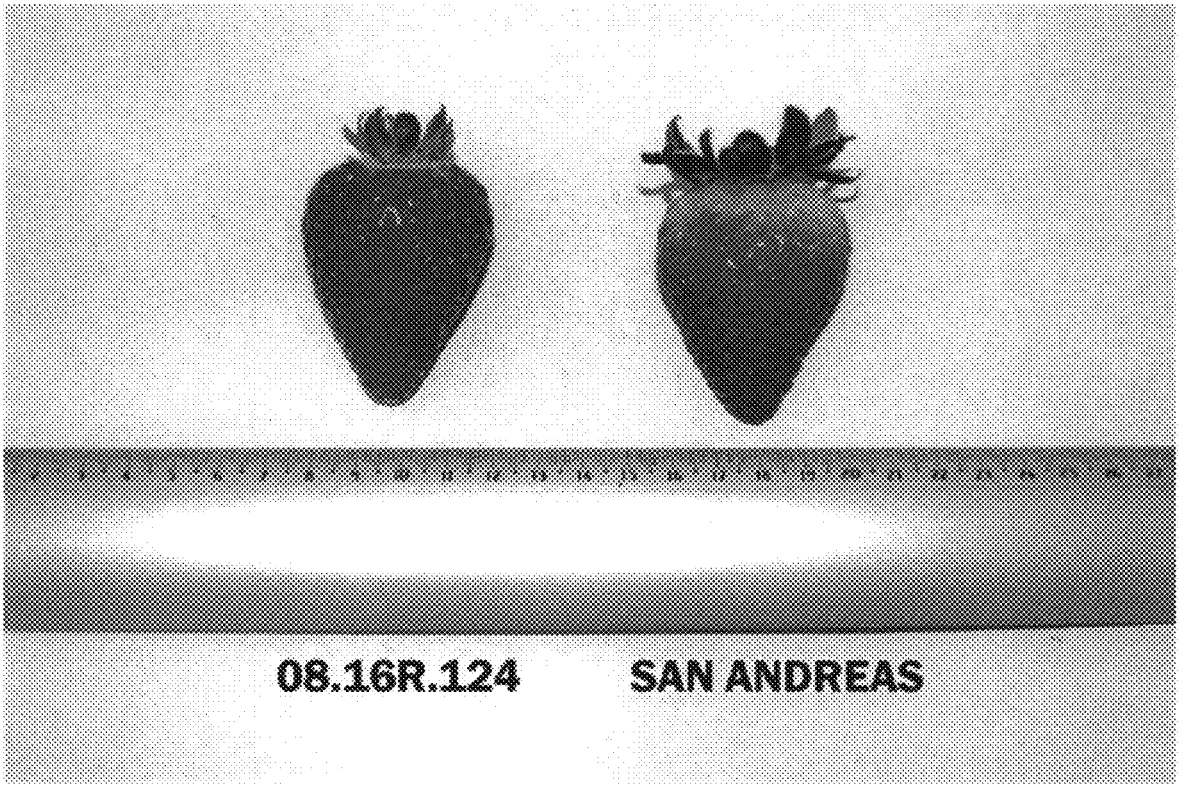

FIG. 16 shows the comparison between whole fruits of the new variety (designated 08.16R.124) and the strawberry variety 'San Andreas' (U.S. Plant Pat. No. 19,975). In it we can see that the attitude of sepals in the fruit of 'San Andreas' (U.S. Plant Pat. No. 19,975) is outwards, whereas the attitude of sepals in the fruit of the new variety (designated 08.16R.124) is upwards.

DESCRIPTION OF THE NEW VARIETY

The following description is in accordance with UPOV terminology and the color terminology herein is in accordance with The Royal Horticultural Society Colour Chart (R.H.S.C.C.), 3rd edition published in 1995.

The color descriptions and other phenotypical descriptions may deviate from the stated values and descriptions depending upon variation in environmental, seasonal, climatic and cultural conditions.

Throughout this specification, color names beginning with a small letter signify that the name of that color, as used in common speech is aptly descriptive. Color names beginning with capital letter designate values based upon The R.H.S. Colour Chart published by he Royal Horticultural society, London, England, 1995.

The following detailed description of the new variety is based upon observations taken of plants and fruits grown under tunnel, in the farm La Mogalla, in Cartaya (Huelva), Spain, 7° W., 37° N., 45 feet elevation (14 meters high).

PROPAGATION

The new variety is principally propagated by way of runners. Although propagation by runners is presently preferred, other known methods of propagating strawberry plants may be used. Strawberries root well after transplanting.

The term "blistering" used herein refers to the texture or rugosity or surface undulation inherent to leaves and is generally a constant characteristic.

'Plared 0822' is a fully remontant variety. 'Plared 0822' is self-fertile. It produces large quantities of pollen throughout the seasons and pollination is generally good as there are very few malformed fruit.

Trials were pursued in the field "La Mogalla" in Cartaya (Huelva), Spain, about 7° W, 37° N, 45 feet elevation (14 meters high). Frigo plants were planted on August 5 (Summer Planted) to produce fruits in autumn and fresh plants were planted on September 25 (Fall Planted) to produce fruits during the spring of following year, with a sample size of two repetitions and 250 plants per repetition in each date of plantation. After planting, plants are grown in raised beds covered with plastic and with small holes in plastic walls, under tunnels. Water and fertilizer are applied through drip irrigation.

GENERAL

TABLE 1

Table 1 shows the Accumulated Fall plantation production of Commercial Quality Fruit (g/plant) of the new variety 'Plared 0822' when compared to its closest varieties 'San Andreas' and 'Albion' (U.S. Plant Pat. No. 16,228) during the months of October, November, and December.

| Variety | 31 Oct. | 30 Nov. | 31 Dec. |
|---|---|---|---|
| Plared 0822 | 65 | 165 | 275 |
| San Andreas | 30 | 109 | 164 |
| Albion | 37 | 117 | 145 |

TABLE 2

Table 2 shows the Accumulated Summer plantation production of Commercial Quality Fruit (g/plant) of the new variety 'Plared 0822' when compared to its closest varieties 'San Andreas' and 'Albion' during the months of March, April, and May.

| Variety | 1 Mar. | 31 Mar. | 27 Apr. | 18 May |
|---|---|---|---|---|
| Plared 0822 | 315 | 635 | 913 | 1271 |
| San Andreas | 116 | 277 | 633 | 824 |
| Albion | 102 | 405 | 580 | 823 |

TABLE 3

Table 3 shows the Total Yield of Fall plantation from October 7 and fruit weight average of the new variety 'Plared 0822' when compared to its closest varieties 'San Andreas' and 'Albion' to December 31.

| Variety | 1st + 2nd Quality Fruit | TOTAL (1st Quality + 2nd Quality) | Weight (g/fruit) |
|---|---|---|---|
| Plared 0822 | 275 + 37 | 312 | 27 – 26 |
| San Andreas | 164 + 25 | 189 | 27 – 26 |
| Albion | 145 + 31 | 176 | 29 – 27 |

TABLE 4

Table 4 shows the Total Yield of Summer plantation from January 2 and fruit weight average of the new variety 'Plared 0822' when compared to its closest varieties 'San Andreas' and 'Albion' to May 18.

| Variety | 1st + 2nd Quality Fruit | TOTAL (1st Quality + 2nd Quality) | Weight (g/fruit) |
|---|---|---|---|
| Plared 0822 | 1271 + 359 | 1630 | 27 – 24 |
| San Andreas | 824 + 191 | 1015 | 27 – 24 |
| Albion | 832 + 222 | 1045 | 30 – 26 |

TABLE 5

Table 5 shows the Production Total of Fall plantation, to December 31 of First Quality Fruit (1st quality) and Second Quality Fruit (2nd quality) in g/plant, of the new variety 'Plared 0822' when compared to its closest varieties 'San Andreas' and 'Albion'.

| Variety | 1st Quality | 2nd Quality | TOTAL (1st Quality + 2nd Quality) | % 2nd Quality |
|---|---|---|---|---|
| Plared 0822 | 275 | 37 | 312 | 11.8 |
| San Andreas | 164 | 25 | 189 | 13.2 |
| Albion | 145 | 31 | 176 | 17.6 |

% 2nd Quality = (2nd Quality/TOTAL) × 100

TABLE 6

Table 6 shows the Production Total of Summer plantation, to May 18 of First Quality Fruit (1st quality) and Second Quality Fruit (2nd quality) in g/plant, of the new variety 'Plared 0822' when compared to its closest varieties 'San Andreas' and 'Albion'.

| Variety | 1st Quality | 2nd Quality | TOTAL (1st Quality + 2nd Quality) | % 2nd Quality |
|---|---|---|---|---|
| Plared 0822 | 1271 | 359 | 1630 | 22.0 |
| San Andreas | 824 | 191 | 1015 | 18.8 |
| Albion | 823 | 222 | 1045 | 21.2 |

% 2nd Quality = (2nd Quality/TOTAL) × 100

TABLE 7

Table 7 shows the Fall plantation Weight (g/Fruit) at two dates: October 31 and December 31 of the new variety 'Plared 0822' when compared to its closest varieties 'San Andreas' and 'Albion'.

| Variety | 31 Oct. WEIGHT (g/fruit) | 31 Dec. WEIGHT (g/fruit) |
|---|---|---|
| Plared 0822 | 27 | 26 |
| San Andreas | 27 | 26 |
| Albion | 29 | 27 |

WEIGHT is shown as the average weight per fruit (g/fruit) in First Quality Fruits.

TABLE 8

Table 8 shows the Summer plantation Weight (g/Fruit) at two dates: March 1 and May 18 of the new variety 'Plared 0822' when compared to its closest varieties 'San Andreas' and 'Albion'

| Variety | 1 Mar. WEIGHT (g/fruit) | 18 May WEIGHT (g/fruit) |
|---|---|---|
| Plared 0822 | 27 | 24 |
| San Andreas | 27 | 24 |
| Albion | 30 | 26 |

WEIGHT is shown as the average weight per fruit (g/fruit) in First Quality Fruits.

TABLE 9

Table 9 shows a comparison of the fruit analysis between the new variety 'Plared 0822' and its closest varieties 'San Andreas' and 'Albion'.

| FRUIT ANALYSIS | Plared 0822 (08.16R.124) | San Andreas | Albion |
|---|---|---|---|
| Firmness (Kg) | 0.80 | 0.70 | 0.80 |
| Humidity & Volatile Matter (%) | 90.40 | 90.50 | 91.30 |
| Dry Matter (%) | 9.60 | 9.50 | 8.70 |
| pH (to 20°) | 3.50 | 3.30 | 3.40 |
| Acidity as Anhydride Citric (%) | 0.83 | 1.02 | 0.74 |
| Soluble Solids (°Brix) | 8.90 | 8.80 | 7.40 |
| Maturity Index | 10.70 | 8.60 | 10.00 |
| Content in Ascorbic Acid (ppm) | 93.30 | 121.00 | 119.6 |
| Dominant Tonality (nm) | 510 | 510 | 500 |
| Luminosity: Transmittance to 460 nm | 43.0 | 35.70 | 31.50 |

The following definitions apply:

Firmness: It is the fruit's resistance to penetration measured in Kilograms (Kg). The measure given has been obtained by the penetrometer ROZE Mod. Arbelette, with a 50 $mm^2$ section head.

Dry Matter: It is the residual weight left from the trituration of the fruit after the drying process at a temperature of 103° C.±2° C. until reaching constant weight.

(%) Dry Matter=(Weight Dry Matter/Weight Fresh Matter)×100

Humidity & Volatile Matter: Represents the content in volatile matters and water of the fruits.

(%) Humidity & Volatile Matter=100−% Dry Matter

Maturity Index: Relation between Soluble solids and Acidity as Anhydride Citric.

Maturity Index=Soluble solids/Acidity as Anhydride Citric

DETAILED DESCRIPTION OF THE NEW VARIETY

The following additional information is provided to further describe the new variety:

Variety: 'Plared 0822'.

Breeder ref: 08.16R.124.

Classification: *Fragaria* x *ananassa* Duchesne ex Rozier.

Plant:

*Growth habit*.—Upright.

*Density of foliage*.—Sparse.

*Vigor*.—Medium.
*Height*.—Medium, about 25 cm.
*Width*.—Medium, about 22 cm.

Leaf:
*Upper side color*.—RHS green group color (near 141 B to 143 A).
*Underside color*.—RHS yellow-green group color (near 147 D to 147 C).
*Length*.—About 9.5 cm.
*Width*.—About 15 cm.
*Shape in cross section*.—Concave.
*Leaf surface undulation or blistering*.—Medium.
*Number of leaflets*.—Three only.
*Glossiness*.—Medium.
*Variegation*.—Absent.

Leaf stem characteristics:
*Color*.—RHS yellow-green group (near 144 B to 145 A).
*Position of hairs*.—Horizontal.
*Length*.—Long, about 19.0 cm to 20.0 cm.

Terminal leaflet:
*Length/width ratio*.—Moderately longer.
*Length*.—Long, about 8.0 cm to 8.5 cm.
*Width*.—Medium, about 7.0 cm to 7.5 cm.
*Shape of base*.—Acute.
*Margin*.—Serrate to crenate.
*Shape in cross section*.—Concave.
*Apex shape*.—Rounded.

Petiole:
*Attitude of hairs*.—Horizontal.
*Color*.—RHS yellow-green group (near 144 B to 145 A).
*Length*.—Long, about 19.0 cm to 20.0 cm.

Stipule:
*Anthocyanin coloration*.—Absent or very weakly expressed, RHS greyed-red group coloration (near 179 C to 179 B).
*Length*.—Short, about 2.0 cm to 2.5 cm.

Stolons:
*Number*.—Medium, about 8.
*Thickness*.—Medium, about 3.0 mm to 3.5 mm.
*Pubescence density*.—Medium.
*Anthocyanin coloration*.—Absent.
*Color*.—RHS yellow-green group (near 145 C to 145 B).
*Length*.—Medium, about 30 cm to 35 cm.

Inflorescence:
*Number of flowers*.—Medium, about 6 to 8.
*Position relative to foliage*.—Above.

Pedicel:
*Attitude/position of hairs*.—Horizontal.
*Average length*.—About 16.5 cm to 17.5 cm.
*Average diameter*.—About 2.8 mm to 3.4 mm.
*Color*.—RHS yellow green group (near 145 C to 145 B).

Flower:
*Diameter/size*.—Medium.
*Size of calyx relative to corolla*.—Larger.
*Arrangement of petals*.—Overlapping.
*Diameter primary flowers*.—Long, about 3.3 cm to 3.7 cm.
*Diameter secondary flowers*.—Medium, about 2.8 cm to 3.2 cm.
*Number of petals*.—About 8 to 9.
*Fragrance*.—No significant fragrance.
*Fall planted*.—Time from bloom to mature fruit (in Huelva, Spain): About 18 days to 20 days.
*Summer planted*.—Time from bloom to mature fruit (in Huelva, Spain): About 27 days to 29 days.
*Stamens*.—Present and numerous with pollen present, fertile and abundant.
*Stamens length*.—Approximately 3.8 mm to 3.9 mm.
*Stamens color*.—RHS white group (near 155 D to 155 C).
*Anthers*.—Generally average in size.
*Anthers color*.—RHS yellow group (near 12 C to 12 B) and darkening with advanced maturity.
*Pollen*.—Fertile and abundant.
*Pollen color*.—RHS yellow orange group (near 16 C to 16 B).
*Pistils*.—Abundant.
*Pistils size*.—Medium.
*Pistils color*.—RHS yellow group (near 13 C to 14 C).

Petal:
*Length/width ratio*.—Equal.
*Length*.—Long, about 10 mm to 12 mm.
*Width*.—Long, about 11 mm to 13 mm.
*Shape*.—Rounded.
*Color of upper side*.—RHS white group (near 155 C to 155 B).
*Base shape*.—Obtuse, becoming narrow.
*Apex shape*.—Rounded.

Sepals:
*Margin type*.—Smooth.
*Apex shape*.—Rounded to ovate.
*Base shape*.—Straight, becoming narrow.

Fruiting truss:
*Attitude*.—Semi-erect.

Fruit:
*Ratio of length/maximum width*.—Moderately longer.
*Color*.—RHS red group (near 44 B to 44 A).
*Peduncle length of inflorescence stem of primary fruit*.—About 19 cm to 21 cm.
*Peduncle length of inflorescence stem of secondary fruit*.—About 14 cm to 16 cm.
*Peduncle of inflorescence stem color*.—RHS yellow-green group (near 145 C to 145 B).

Primary fruit:
*Length*.—Long, about 5.5 cm to 6.1 cm.
*Width*.—Medium, about 4.4 cm to 4.8 cm.

Secondary fruit:
*Length*.—Long, about 4.8 cm to 5.3 cm.
*Width*.—Medium, about 3.5 cm to 4.0 cm.

Primary and secondary fruit:
*Size*.—Medium to large.
*Shape*.—Conical.
*Difference in shapes between primary and secondary fruits*.—None to very slight.
*Width of band without achenes*.—Absent or very narrow.
*Color of achenes*.—RHS orange to orange-red group (near 31 B to 32 C).
*Evenness of surface*.—Even or very slightly uneven.
*Evenness of color*.—Even or very slightly uneven.
*Glossiness*.—Medium.
*Insertion/position of achenes*.—Below surface.
*Insertion of calyx*.—Inserted.
*Attitude of sepals*.—Upwards.
*Size/diameter of calyx in relation to diameter of fruit*.—Slightly larger. The calyx presents 7 to 8 sepals with lanceolate shape and 4 to 5 sepals in addition smaller than above mentioned with pointed shape.

*Color upper side of sepals*.—Green group (near 139 B to 139 A).

*Color underside of sepals*.—Yellow-green group (near 143 C to 143 B).

*Length of sepals*.—Long, about 17 mm to 20 mm.

*Width of sepals*.—Long, about 8 mm to 10 mm.

*Adherence of calyx*.—Medium.

*Firmness*.—Firm.

*Color of flesh* (*excluding core*).—RHS orange-red (RHS orange-red group near 34 B to 34 A), lightening toward center.

*Distribution of orange red color of flesh*.—Marginal.

*Fruit cavity/hollow center*.—Small to medium.

*Color of core*.—RHS orange-red group (near 31 B to 31 A).

*Sweetness*.—Medium. 8.90° Brix.

*Acidity*.—Medium. 0.83%.

*Time of flowering* (50% *of plants at first flower*).—Very early.

*Time of ripening* (50% *of plants with ripe fruits*).—Very early.

*Type of bearing*.—Fully remontant.

Disease resistance: No particular sensitivity to any disease or parasite has been observed for 'Plared 0822'.

Storage qualities: 'Plared 0822' fruit maintain their quality characteristics when keeping them in a frigo chamber at temperatures of about 2° C. during 48 hours. The fruit's color remains substantially the same.

Shipping quality: 'Plared 0822' fruit maintains their quality characteristics when shipped in frigo conditions at temperatures of about 2° C. during 48 hours.

Fruit storage: 'Plared 0822' fruit life is medium at about 6 to 8 days at temperatures of about 4 to 5° C.

Fruit market use: 'Plared 0822' fruits are suitable for consumption as fresh fruit. Also, they are amenable to processing.

Fall planted:

Planting date: August 5 in the farm of La Mogalla, in Cartaya (Huelva), Spain, about 7° W, 37° N, 45 feet elevation (15 meters high).

Time of flowering data: 10% Flowering (based on August 5 planting date): About September 10.

First mature fruits (based on August 5 planting date): About September 29.

Maturity (15-20 g/plant) (based on August 5 planting date): About October 13.

Time of flowers (50% of plants at first flower) (based on August 5 planting date): About September 20.

Time of ripening (based on August 5 planting date): After planting as aforesaid, plants are grown in raised beds covered with plastic and with small holes in plastic walls, under tunnel. Water and fertilizer were applied through drip irrigation. Time of ripening (50% of plants with ripe fruit) is about October 7. First mature fruit is about September 29, and maturity (15-20 g/plant) is about October 13.

Summer planted:

Planting date: September 25 in the farm of La Mogalla, in Cartaya (Huelva), Spain, about 7° W, 37° N, 45 feet elevation (15 meters high).

Time of flowering data: 10% Flowering (based on September 25 planting date): About November 1.

First mature fruits (based on September 25 planting date): About December 1.

Maturity (15-20 g/plant) (based on September 25 planting date): About January 7.

Time of flowers (50% of plants at first flower) (based on September 25 planting date): About October 13.

Time of ripening (based on September 25 planting date): After planting as aforesaid, plants are grown in raised beds covered with plastic and with small holes in plastic walls, under tunnel. Water and fertilizer were applied through drip irrigation. Time of ripening (50% of plants with ripe fruit) is about December 27. First mature fruit is about December 1, and maturity (15-20 g/plant) is about January 7.

I claim:

1. A new and distinct strawberry plant of the variety substantially as shown and described.

* * * * *